United States Patent
Oya et al.

(10) Patent No.: US 8,187,436 B2
(45) Date of Patent: May 29, 2012

(54) SENSOR DETERIORATION JUDGING APPARATUS AND SENSOR DETERIORATION JUDGING METHOD

(75) Inventors: Seiji Oya, Aichi (JP); Tomohiro Wakazono, Kounan (JP); Koji Shiotani, Kasugai (JP); Tomonori Kondo, Kounan (JP); Mineji Nasu, Kounan (JP); Hiroshi Kubota, Wako (JP); Kazuo Yanada, Wako (JP); Koichi Awano, Wako (JP)

(73) Assignees: NGK Spark Plug Co., Ltd., Aichi (JP); Honda Motor Co., Ltd., Tokyo (JP)

( * ) Notice: Subject to any disclaimer, the term of this patent is extended or adjusted under 35 U.S.C. 154(b) by 1522 days.

(21) Appl. No.: 11/603,018

(22) Filed: Nov. 22, 2006

(65) Prior Publication Data

US 2007/0119709 A1    May 31, 2007

(30) Foreign Application Priority Data

Nov. 25, 2005 (JP) ................ P2005-340537

(51) Int. Cl.
*G01N 27/409* (2006.01)
*G01N 27/417* (2006.01)
(52) U.S. Cl. .............. 204/421; 205/783.5
(58) Field of Classification Search ........ 204/410, 204/411, 421–429; 205/781, 783.5–785, 205/787; 73/23.31, 23.32
See application file for complete search history.

(56) References Cited

U.S. PATENT DOCUMENTS

| | | | | |
|---|---|---|---|---|
| 5,209,206 A | * | 5/1993 | Danno et al. | 123/479 |
| 6,099,717 A | * | 8/2000 | Yamada et al. | 205/784.5 |
| 6,120,663 A | | 9/2000 | Kato et al. | |
| 6,383,354 B1 | * | 5/2002 | Kurokawa et al. | 204/425 |
| 2004/0238378 A1 | * | 12/2004 | Kumazawa et al. | 205/781 |

FOREIGN PATENT DOCUMENTS

| | | |
|---|---|---|
| JP | 11-14589 | 1/1999 |
| WO | 03/083465 | 10/2003 |

* cited by examiner

*Primary Examiner* — Alex Noguerola
*Assistant Examiner* — Gurpreet Kaur
(74) *Attorney, Agent, or Firm* — Morgan, Lewis & Bockius LLP

(57) ABSTRACT

A gas sensor controller 190 stops an operation of pumping in or out oxygen that is being performed by a first pump cell 111 in a state that the oxygen concentration (oxygen partial pressure) of a gas to be measured is equal to a status judgment reference value (20%). The gas sensor controller 190 calculates an oxygen pressure in a second measurement chamber 161 on the basis of a second pump current Ip2. If the oxygen pressure in the second measurement chamber 161 is equal to a deterioration judgment reference value, the gas sensor controller 190 judges that the second pump cell 113 is in a normal state. If the oxygen pressure in the second measurement chamber 161 is different from the deterioration judgment reference value, the gas sensor controller 190 judges that the second pump cell 113 is in a deteriorated state.

4 Claims, 3 Drawing Sheets

SENSOR DETERIORATION JUDGING APPARATUS AND SENSOR DETERIORATION JUDGING METHOD

BACKGROUND OF THE INVENTION

1. Field of the Invention

The present invention relates to a sensor deterioration judging apparatus and a sensor deterioration judging method for judging whether a gas sensor is in a deteriorated state.

2. Description of the Related Art

A gas sensor is known which is equipped with a first measurement chamber, a first oxygen ion pump cell, a second measurement chamber, a second oxygen ion pump cell, a reference oxygen chamber, and an oxygen partial pressure detection cell.

Various apparatus for judging the state of such a gas sensor have been proposed which measure currents flowing through various cells of the gas sensor, output voltages of cells, impedances of cells, or like parameters and detects a failure state of the gas sensor on the basis of whether or not measurement results are within allowable ranges (refer to JP-A-11-014589 (corresponding to U.S. Pat. No. 6,120,663) and WO-A-03/083465, for example).

3. Problems to be Solved by the Invention

However, the above conventional apparatus have a problem that they cannot detect a deteriorated state of a gas sensor such as low sensitivity of a cell though they can detect fatal failure states such as a line disconnection and short-circuiting among various states of a gas sensor.

In a gas sensor having a fatal failure, the values of currents, voltages, impedances, etc. of various cells are clearly out of the ranges of those of a normal gas sensor. Therefore, a failure state of a gas sensor can be detected by the above conventional apparatus.

In contrast, in a deteriorated gas sensor, the values of currents, voltages, impedances, etc. of various cells are approximately in the same ranges as those of a normal gas sensor. Therefore, it is difficult to discriminate a deteriorated state from a normal state on the basis of the above values. Therefore, it is difficult for the above conventional apparatus to detect a deteriorated state of a gas sensor.

Having a different a gas detection characteristic than in a normal state, a gas sensor in a deteriorated state cannot produce the same gas detection result as in the normal state and hence may be lowered in gas detection accuracy.

The present invention has been made in view of the above problem, and an object of the invention is to provide a sensor deterioration judging apparatus and a sensor deterioration judging method capable of judging whether a gas sensor having various cells is in a deteriorated state.

SUMMARY OF THE INVENTION

The invention, which has been made to attain the above object, provides a sensor deterioration judging apparatus for judging whether a gas sensor is in a deteriorated state, the gas sensor including:

a first measurement chamber into which a gas to be measured is introduced through a first diffusion resistor portion;

a first oxygen ion pump cell having a first oxygen ion conductor and first and second electrodes provided on the first oxygen ion conductor wherein the first electrode is arranged in the first measurement chamber which pumps oxygen into or out of the gas that has been introduced into the first measurement chamber to be measured;

a second measurement chamber into which the gas to be measured is introduced through a second diffusion resistor portion after having been subjected to oxygen pumping in the first measurement chamber;

a second oxygen ion pump cell having a second oxygen ion conductor and third and fourth electrodes provided on the second oxygen ion conductor wherein the third electrode is arranged in the second measurement chamber so that a current corresponding to a concentration of the gas to be measured in the second measurement chamber flows in the second oxygen ion pump cell;

a reference oxygen chamber set to have a reference oxygen partial pressure atmosphere; and an oxygen partial pressure detection cell having a third oxygen ion conductor and fifth and sixth electrodes provided on the third oxygen ion conductor wherein the fifth electrode is provided in the first measurement chamber and the sixth electrode is provided in the reference oxygen chamber, the sensor deterioration judging apparatus characterized by comprising a first pump current detecting unit for detecting a first pump current flowing through the first oxygen ion pump cell; a status judging unit for determining an oxygen partial pressure of the gas to be measured on the basis of the first pump current, and for judging whether the determined oxygen partial pressure of the gas to be measured is equal to a preset status judgment reference value; a pump stopping unit for stopping the pumping in or out of oxygen that is being performed by the first oxygen ion pump cell when the status judging unit judges that the oxygen partial pressure of the gas to be measured is equal to the status judgment reference value; a second pump current detecting unit for detecting a second pump current flowing through the second oxygen ion pump cell after the pump stopping unit stops the pumping operation of the first oxygen ion pump cell; and a deterioration judging unit for judging that the second oxygen ion pump cell is in a deteriorated state when an oxygen partial pressure in the second measurement chamber calculated on the basis of the second pump current differs from a deterioration judgment reference value that is set in advance on the basis of the status judgment reference value.

The invention, which has been made to attain the above object, also provides a sensor deterioration judging method for judging whether a gas sensor is in a deteriorated state, the gas sensor having a first measurement chamber into which a gas to be measured is introduced through a first diffusion resistor portion; a first oxygen ion pump cell having a first oxygen ion conductor and first and second electrodes arranged on the first oxygen ion conductor wherein the first electrode is provided in the first measurement chamber for pumping oxygen into or out of the gas to be measured that has been introduced into the first measurement chamber; a second measurement chamber into which the gas to be measured after having been subjected to the oxygen pumping in the first measurement chamber; a second oxygen ion pump cell having a second oxygen ion conductor and third and fourth electrodes provided on the second oxygen ion conductor wherein the third electrode is provided in the second measurement chamber so that a current corresponding to a concentration of the gas to be measured in the second measurement chamber flows in the second oxygen ion pump cell; a reference oxygen chamber set to have a reference oxygen partial pressure atmosphere; and an oxygen partial pressure detection cell having a third oxygen ion conductor and fifth and sixth. electrodes provided on the third oxygen ion conductor so that the fifth electrode is provided in the first measurement chamber and the sixth electrode is provided in the reference oxygen chamber, the sensor deterioration judging method characterized by comprising the steps of detecting a first pump current flowing through the first oxygen ion pump cell; determining an oxygen partial pressure of the gas to be measured on the basis of the first pump current, and judging whether or not the determined oxygen partial pressure of the gas to be measured is equal to a preset status judgment reference value; stopping the first oxygen ion pump cell from the pumping in or out of oxygen when the oxygen partial pressure of the gas to be measured is equal to the status judgment reference value; detecting a second pump current flowing through the second oxygen ion pump cell after the pumping operation of the first oxygen ion pump cell is stopped; and judging that the second oxygen ion pump cell is in a deteriorated state when an oxygen partial pressure in the second measurement chamber that is calculated on the basis of the second pump current differs from a deterioration judgment reference value that is set in advance on the basis of the status judgment reference value.

First, an operation of pumping in or out oxygen that is being performed by the first oxygen ion pump cell is stopped in a state that the oxygen partial pressure in a gas to be measured is equal to the status judgment reference value. As a result, part of the gas existing in the first measurement chamber moves to the second measurement chamber, whereby the oxygen partial pressure in the second measurement chamber comes close to the partial pressure in the first measurement chamber (i.e., the deterioration judgment reference value which is set in advance on the basis of the status judgment reference value).

After the oxygen partial pressure in the second measurement chamber is set to the deterioration judgment reference value, a current corresponding to the deterioration judgment reference value flows through the second oxygen ion pump cell if the second oxygen ion pump cell is in a normal state. In contrast, if the second oxygen ion pump cell is in a deteriorated state, a current that is smaller than the normal-state current corresponding to the deterioration judgment reference value flows through the second oxygen ion pump cell.

Therefore, whether the second oxygen ion pump cell is in a deteriorated state can be judged by judging whether or not an oxygen partial pressure calculated on the basis of a second pump current that is detected in a state that the oxygen partial pressure in the second measurement chamber is set at the deterioration judgment reference value is equal to the deterioration judgment reference value.

In the invention, if the oxygen partial pressure in the second measurement chamber that is calculated on the basis of the second pump current is different from the deterioration judgment reference value, the second oxygen ion pump cell is judged to be in a deteriorated state.

As described above, the sensor deterioration judging apparatus and the sensor deterioration judging method according to the invention can judge whether or not the second oxygen ion pump cell is in a deteriorated state and hence can judge whether or not the gas sensor having the various cells is in a deteriorated state.

Incidentally, it may take a certain time for the oxygen partial pressure in the second measurement chamber to become stable after a pumping operation of the first oxygen ion pump cell is stopped by the pump stopping unit.

In view of this, the above sensor deterioration judging apparatus may be such that the second pump current detecting unit detects a second pump current after a lapse of a stabilization standby time, the stabilization standby time being the time that the oxygen partial pressure in the second measurement chamber takes to become stable after the pumping operation of the first oxygen ion pump cell is stopped by the pump stopping unit.

After the stabilization standby time has elapsed since a pumping operation of the first oxygen ion pump cell was stopped, the oxygen partial pressure in the second measurement chamber can reliably be set equivalent to that in the first measurement chamber. As a result, the deterioration judging unit can judge, with higher accuracy, whether or not the second oxygen ion pump cell is in a deteriorated state.

Therefore, the invention makes it possible to judge, with higher accuracy, whether or not the second oxygen ion pump cell is in a deteriorated state and hence to increase the judgment accuracy in judging whether or not the gas sensor is in a deteriorated state.

DESCRIPTION OF REFERENCE NUMERALS

Figure 1:
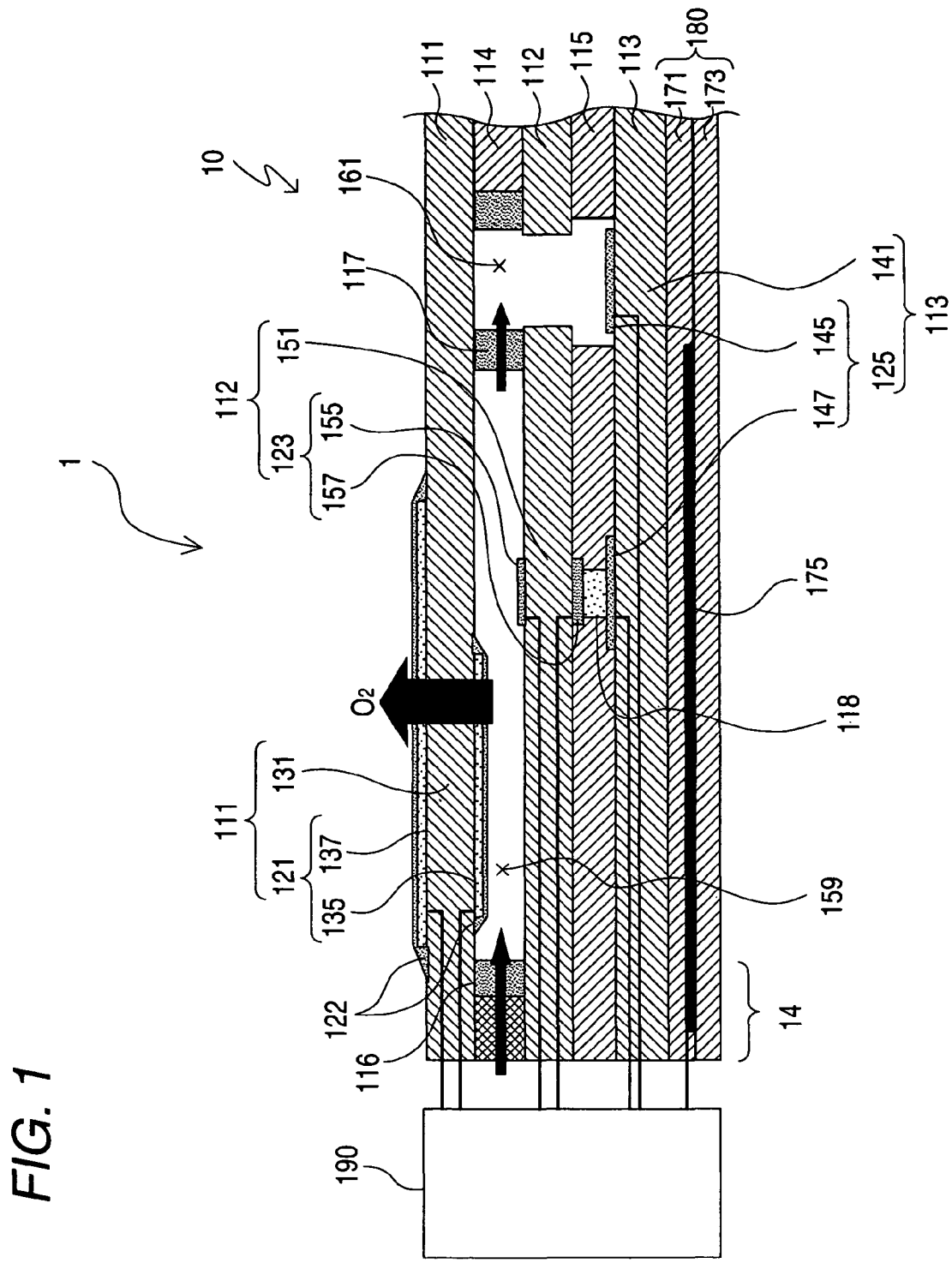
FIG. 1 schematically shows the configuration of a gas detecting apparatus having a gas sensor controller.

Reference numerals used to identify various structural features in the drawings include the following.

1 . . . Gas detecting apparatus; 10 . . . NOx gas sensor; 111 . . . First pump cell; 112 . . . Oxygen partial pressure detection cell; 113 . . . Second pump cell; 118 . . . Reference oxygen chamber; 159 . . . First measurement chamber; 161 . . . Second measurement chamber; 180 . . . Heater unit; 190 . . . Gas sensor controller.

DETAILED DESCRIPTION OF THE INVENTION

An embodiment of the present invention will be hereinafter described with reference to the drawings.

FIG. 1 schematically shows the configuration of a gas detecting apparatus 1 having a gas sensor controller 190 to which the invention is applied.

The gas detecting apparatus 1 is equipped with the gas sensor controller 190 and an NOx gas sensor 10, and is used for, for example, the purpose of detecting a particular gas (in this embodiment, NOx) contained in an exhaust gas of various combustion apparatus such as an automobile internal combustion engine and a boiler.

The gas sensor controller 190 has, as a main component, a microcomputer that is equipped with a central processing unit (CPU), a RAM, a ROM, a signal input/output section, etc. The gas sensor controller 190 performs processing of drive-controlling the NOx gas sensor 10, processing of detecting the particular gas contained in an exhaust gas on the basis of a detection signal of the NOx gas sensor 10, sensor diagnosis processing (on-board diagnosis (OBD)) of judging whether the NOx gas sensor 10 is in a deteriorated state, and other processing.

In FIG. 1, the NOx gas sensor 10 is drawn as a sectional view showing its internal configuration. In the following description, the left-hand side and the right-hand side of the NOx gas sensor 10 will be referred to as "tip side" and "rear side," respectively. FIG. 1 shows the internal configuration of a tip-side portion of the NOx gas sensor 10, that is, its rear-side portion is omitted in FIG. 1.

First, the NOx gas sensor 10 will be described.

The NOx gas sensor 10 is configured in such a manner that a first pump cell 111, an oxygen partial pressure detection cell 112, and a second pump cell 113 are laid one on another via insulating layers 114 and 115 which are mainly made of alumina. In the NOx gas sensor 10, a heater unit 180 is laid on the second pump cell 113 on the side opposite to the cells 111 and 112.

Among the cells 111-113, the first pump cell 111 is composed of a first solid electrolyte layer 131 made of zirconia which is oxygen-ion-conductive and a pair of first porous electrodes 121 that are a first electrode 135 and a second electrode 137 between which the first solid electrolyte Layer 131 is sandwiched. Each of the first electrode 135 and the second electrode 137 is made of platinum, a platinum alloy, cermet which contains platinum and ceramics (e.g., a solid electrolyte), or a like material. A protective layer 122 made of a porous material is formed on the surface of each of the first electrode 135 and the second electrode 137.

The second pump cell 113 is composed of a second solid electrolyte layer 141 made of zirconia which is oxygen-ion-conductive and a pair of second porous electrodes 125 that are a third electrode 145 and a fourth electrode 147 which are formed on that surface of the second solid electrolyte layer 141 which faces the insulating layer 115.

Each of the third electrode 145 and the fourth electrode 147 is made of platinum, a platinum alloy, cermet which contains platinum and ceramics (e.g., a solid electrolyte), or a like material.

The oxygen partial pressure detection cell 112 is composed of a third solid electrolyte layer 151 made of zirconia which is oxygen-ion-conductive and a pair of detection porous electrodes 123 that are a fifth electrode 155 and a sixth electrode 157 between which the third solid electrolyte layer 151 is sandwiched. Each of the fifth electrode 155 and the sixth electrode 157 is made of platinum, a platinum alloy, cermet which contains platinum and ceramics (e.g., a solid electrolyte), or a like material.

A first measurement chamber 159 into which a gas to be measured is to be introduced is formed inside the NOx gas sensor 10. A gas to be measured is introduced externally into the first measurement chamber 159 through a first diffusion resistor 116 which is disposed between the first pump cell 111 and the oxygen partial pressure detection cell 112.

The first diffusion resistor 116 is made of a porous material and disposed in a gas to be measured introduction passage 14 extending from the tip-side opening of the NOx gas sensor 10 to the first measurement chamber 159. As such, the first diffusion resistor 116 restricts the introduction amount (passage amount) per unit time of a gas to be measured being introduced into the first measurement chamber 159.

The introduction passage 14 is a region, located on the tip side (left side in FIG. 1) of the first measurement chamber 159, of the space surrounded by the first pump cell 111 and the oxygen partial pressure detection cell 112. The first electrode 135 (covered with the protective layer 122) of the first pump cell 111 and the fifth electrode 155 of the oxygen partial pressure detection cell 112 face the first measurement chamber 159.

A second diffusion resistor 117 made of a porous material is disposed on the rear side (right side in FIG. 1) of the first measurement chamber 159, and a second measurement chamber 161 is formed between the third electrode 145 and the second diffusion resistor 117. The second measurement chamber 161 is formed so as to penetrate through the oxygen partial pressure detection cell 112 in the lamination direction.

In addition to the second measurement chamber 161, a reference oxygen chamber 118 is formed inside the NOx gas sensor 10. The reference oxygen chamber 118 is formed between the third solid electrolyte layer 151 of the oxygen partial pressure detection cell 112 and the second solid electrolyte layer 141 of the second pump cell 113. The second measurement chamber 161 and the reference oxygen chamber 118 are arranged in this order-in the direction from the rear side to the tip side along the second pump cell 113. A prescribed oxygen partial pressure atmosphere (to serve as a concentration detection reference) is set in the reference oxygen chamber 118.

The sixth electrode 157 of the oxygen partial pressure detection cell 112 and the fourth electrode 147 of the second pump cell 113 face the reference oxygen chamber 118.

The heater unit 180 is formed by laminating sheet-like insulating layers 171 and 173 which are made of insulative ceramics such as alumina. The heater unit 180 is provided with a heater 175 which is mainly made of platinum and sandwiched between the insulating layers 171 and 173.

In the NOx gas sensor 10 having the above configuration, the first pump cell 111 can pump oxygen into and out of the first measurement chamber 159. The oxygen partial pressure detection cell 112 can measure the difference between the oxygen concentration (oxygen partial pressure) in the first measurement chamber 159 and the oxygen concentration (oxygen partial pressure) in the reference oxygen chamber 118 which is controlled to a constant value; that is, the oxygen partial pressure detection cell 112 can measure the oxygen concentration (oxygen partial pressure) in the first measurement chamber 159.

The NOx gas sensor 10 is driven by the gas sensor controller 190 which is provided separately. The heater 175 is driven by the gas sensor controller 190, whereby the temperature of each of the first pump cell 111, the second pump cell 113, arid the oxygen partial pressure detection cell 112 is increased to an activation temperature.

The gas sensor controller 190 drive-controls the heater 175 so that the temperature of the NOx gas sensor 10 is increased to the activation temperature (e.g., 750° C.). In this state, the gas sensor controller 190 controls a first pump current Ip1 flowing through the first pump cell 111 so that a voltage Vs across the oxygen partial pressure detection cell 112 becomes equal to a preset constant voltage (e.g., 425 mV).

While controlling the first pump current Ip1, the gas sensor controller 190 applies a predetermined second pump voltage Vp2 (e.g., 450 mV) to the second pump cell 113. As a result, in the second measurement chamber 161, NOx is dissociated (reduced) with catalyst action of the pair of second porous electrodes 125 of the second pump cell 113. Resulting oxygen ions move through the second solid electrolyte layer 141 between the third electrode 145 and the fourth electrode 147, whereby a second pump current Ip2 flows. That is, the second pump cell 113 dissociates particular gas components (NOx (nitrogen oxides) to be detected that exist in the second measurement chamber 161 and pumps oxygen from the second measurement chamber 161 to the reference oxygen chamber 118.

Oxygen ions ($O^{2-}$) produced at the third electrode 145 in the second measurement chamber 161 move to the fourth electrode 147 via the second solid electrolyte layer 141, and oxygen molecules ($O_2$) are emitted from the fourth electrode 147.

That is, connected to the NOx gas sensor 10, the gas sensor controller 190 performs processing of adjusting the oxygen concentration (oxygen partial pressure) in the first measurement chamber 159 through a pumping operation of the first pump cell 111, setting the oxygen concentration (oxygen partial pressure) in the second measurement chamber 161 to an NOx detection concentration that enables NOx detection, and detecting NOx on the basis of the magnitude, integration value, or the like of the second pump current Ip2.

Figure 2:
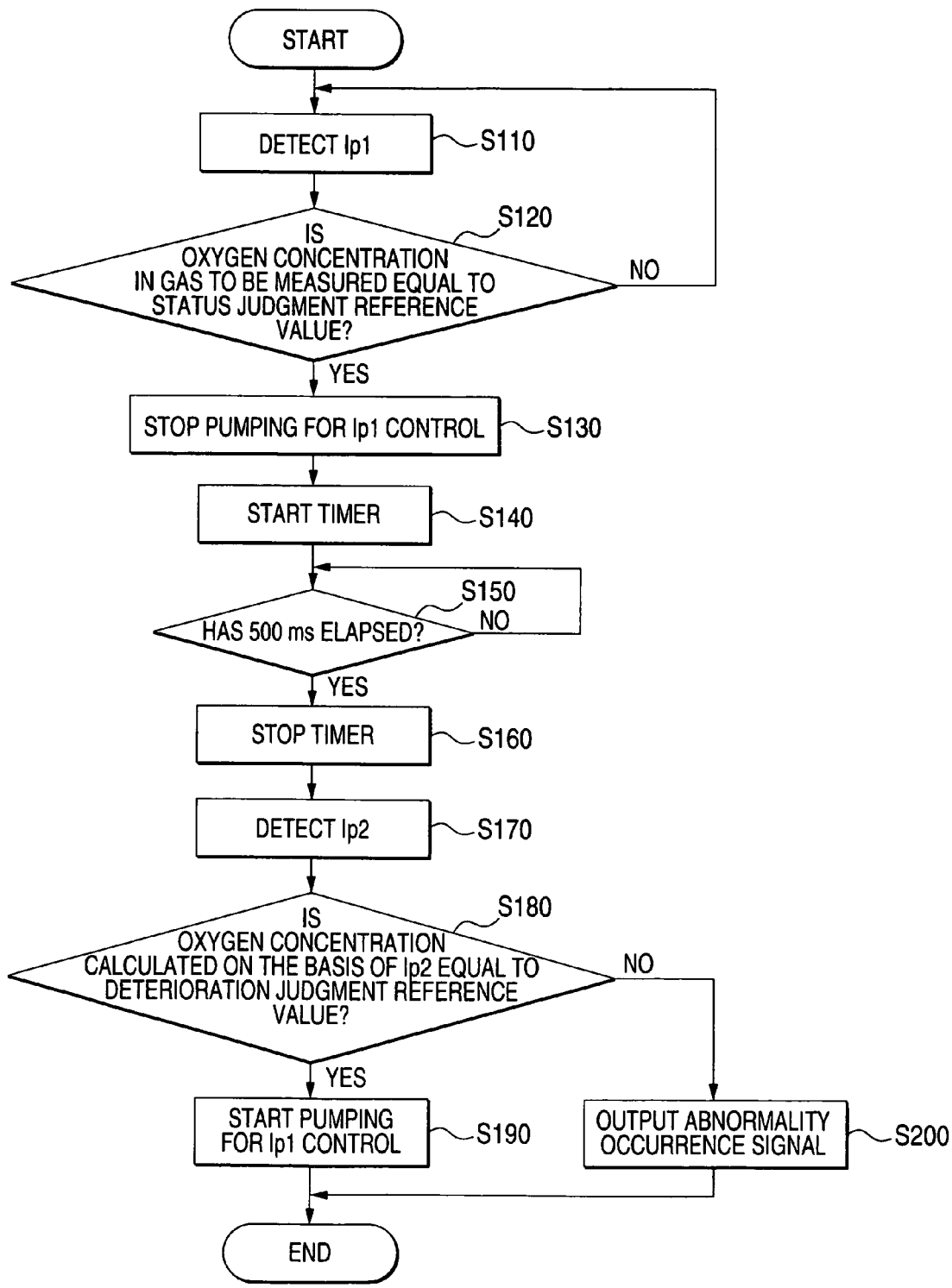
FIG. 2 is a flowchart showing the details of a sensor diagnosis process.

Next, the details of a sensor diagnosis process (on-board diagnosis (OBD)) which is executed by the gas sensor controller 190 will be described. FIG. 2 is a flowchart showing the details of the sensor diagnosis process.

It is desirable that the sensor diagnosis process be executed with such timing that the oxygen concentration (oxygen partial pressure) in an exhaust gas is high, such as immediately after a start of the gas sensor controller 190 or during a fuel-cut operation.

After a start of the sensor diagnosis process, first, at step S110, a current is caused to flow through the first pump cell 111 so that the voltage Vs across the oxygen partial pressure detection cell 112 becomes equal to a predetermined constant voltage (e.g., 425 mV). In this state, a first pump current Ip1 flowing through the first pump cell 111 is detected.

An oxygen concentration (oxygen partial pressure) in a gas to be measured can be detected on the basis of the first pump current Ip1.

At The next step S120, an oxygen concentration (oxygen partial pressure) in a gas to be measured is determined on the basis of the first pump current Ip1 that was detected at step S110 and it is judged whether or not the determined oxygen partial pressure of the gas to be measured is equal to a predetermined status judgment reference value. If the judgment result is affirmative, the process moves to step S130. If the judgment result is negative, the above steps are executed again as standby processing.

The status judgment reference value is set higher than an oxygen partial pressure in the second measurement chamber 161 to be set at the time of detection of the particular gas. In this embodiment, the status judgment reference value is set at 20% (equivalent to the oxygen partial pressure in the atmosphere).

If an affirmative judgment is made at step S120, the process moves to step S130, where the operation of pumping oxygen into or out of the first measurement chamber 159 that is being performed by the first pump cell 111 is stopped. As a result, oxygen is no longer pumped out of the first measurement chamber 159 and hence the oxygen concentration (oxygen partial pressure) in the first measurement chamber 159 does not decrease.

At the next step S140, timer processing for measuring an elapsed time is started.

At the ensuing step S150, it is judged whether or not 500 ms has elapsed since the start of the time measurement of the timer processing. If the judgment result is affirmative, the process moves to step S160. If the judgment result is negative, step S150 is performed again as standby processing.

Figure 3:
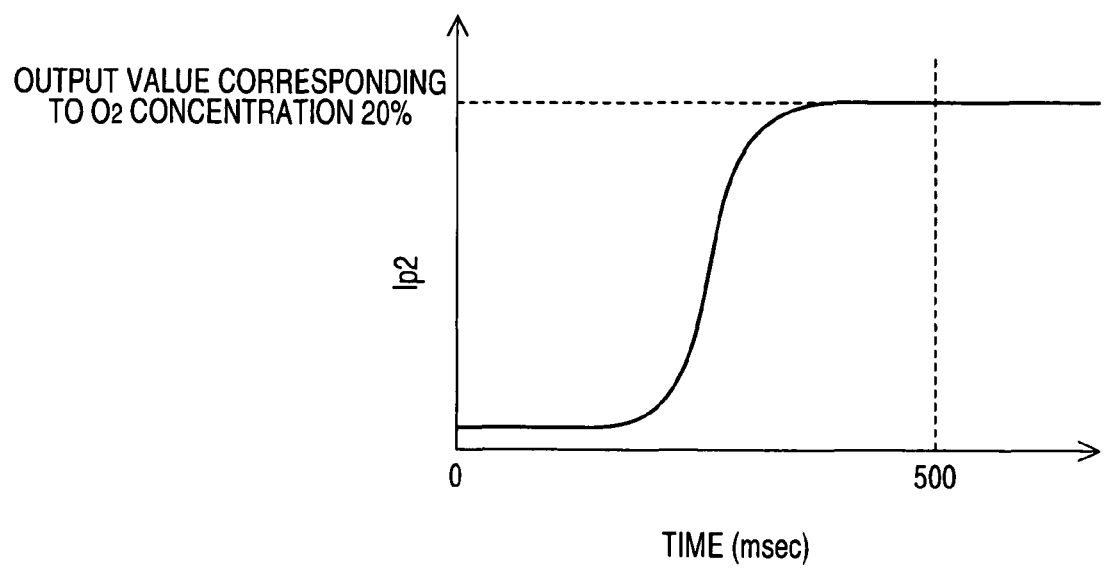
FIG. 3 shows a result of measurement of a second pump current which flows through a second pump cell in a state that air has been introduced into a first measurement chamber and oxygen pumping by a first pump cell is stopped.

FIG. 3 shows a result of measurement of a second pump current Ip2 which flows through the second pump cell 113 in a situation that air (oxygen partial pressure: 20%) was introduced into the first measurement chamber 159 and oxygen pumping by the first pump cell 111 was stopped. FIG. 3 shows a waveform of the second pump current Ip2 as a measurement result in a coordinate plane in which the vertical axis represents the second pump current Ip2 and the horizontal axis represents the elapsed time.

As shown in FIG. 3, the second pump current Ip2 is almost constant in a period from the stop of oxygen pumping by the first pump cell 111 (time=0 s) to a time point when about 200 ms elapses, because in that period the second diffusion resistor 117 restricts the rate of gas inflow from the first measurement chamber 159 to the second measurement chamber 161. As the gas thereafter flows from the first measurement chamber 159 to the second measurement chamber 161, the second pump current Ip2 increases gradually. The second pump current Ip2 reaches an output value (current value) corresponding to an oxygen concentration (oxygen partial pressure) 20% at or before a time point when the elapsed time becomes 500 ms.

This indicates that the gas atmosphere (oxygen partial pressure) in the second measurement chamber 161 becomes equivalent to that in the first measurement chamber 159 when at least 500 ms has elapsed since the stop of oxygen pumping by the first pump cell 111.

If an affirmative judgment is made at step S150, the process moves to step S160, where the timer processing of measuring the elapsed time is stopped.

At the next step S170, a second pump current Ip2 flowing through the second pump cell 113 is detected.

A second pump voltage Vp2 is applied to the second pump cell 113 and the second pump current Ip2 corresponds to an oxygen partial pressure in the second measurement chamber 161.

At the next step S180, an oxygen concentration (oxygen partial pressure) in the second measurement chamber 161 is calculated on the basis of the second pump current Ip2 detected at step S170 and it is judged whether or not the calculated oxygen partial pressure in the second measurement chamber 161 is equal to a predetermined deterioration judgment reference value. If the judgment result is affirmative, the process moves to step S190. If the judgment result is negative, the process moves to step S200.

That is, at step S180, if the oxygen partial pressure in the second measurement chamber 161 is equal to the deterioration judgment reference value, it is judged that the second pump cell 113 is in a normal state. If the oxygen partial pressure in the second measurement chamber 161 is different from the deterioration judgment reference value, it is judged that the second pump cell 113 is in a deteriorated state.

The deterioration judgment reference value which is used in the judgment of step S180 is set at ⅔ (about 13%) of the status judgment reference value (20%) which is used in the judgment of step S120.

That is, in this embodiment, the second pump cell 113 is judged to be in a deteriorated state if an oxygen partial pressure in the second measurement chamber 161 which is calculated on the basis of a second pump current Ip2 is lower than ⅔ (about 13%; deterioration judgment reference value) of the status judgment reference value (20%).

If an affirmative judgment is made at step S180, the process moves to step S190, where pumping of oxygen into or out of the first measurement chamber 159 by the first pump cell 111 is started again. That is, the processing of controlling the first pump current Ip1 flowing through the first pump cell 111 so that the voltage Vs across the oxygen partial pressure detection cell 112 becomes equal to the constant voltage (e.g., 425 mV) is restarted.

As a result, the oxygen partial pressure in each of the first measurement chamber 159 and the second measurement chamber 161 is set to a particular gas detection concentration (e.g., a low concentration), whereby the NOx gas sensor 10 is rendered in a state that it is capable of NOx detection.

The gas sensor controller 190 detects a second pump current Ip2 of the NOx gas sensor 10 by executing an NOx detection process which is an internal process separate from the sensor diagnosis process. The gas sensor controller 190 performs NOx detection on the basis of the detected second pump current Ip2.

If a negative judgment is made at step 5180, the process moves to step S200, where an abnormality occurrence signal indicating that the second pump cell 113 is in a deteriorated state is output from an output terminal (not shown) of the gas sensor controller 190 to an external apparatus.

The external apparatus which has received the abnormality occurrence signal performs processing of informing a user that the NOx gas sensor 10 is in a deteriorated state. Specific examples of this processing is processing of turning on a warning lamp for indicating that the NOx gas sensor 10 is in a deteriorated state and processing of outputting a voice message to the same effect.

When step S190 or S200 has been executed, this control process (sensor diagnosis process) is finished.

As described above, the gas sensor controller 190 of the gas detecting apparatus 1 according to the embodiment stops an operation of pumping in or out oxygen that is being performed by the first pump cell 111 (S130) in a state that the oxygen concentration (oxygen partial pressure) of a gas to be measured is equal to the status judgment reference value (20%) (S120: yes). As a result, part of the gas existing in the first measurement chamber 159 moves to the second measurement chamber 161, whereby the oxygen partial pressure in the second measurement chamber 161 comes close to that in the first measurement chamber 159.

After the oxygen partial pressure in the second measurement chamber 161 is set to the deterioration judgment reference value (13%), a current corresponding to the deterioration judgment reference value flows through the second pump cell 113 if the second pump cell 113 is in a normal state. In contrast, if the second pump cell 113 is in a deteriorated state, the catalyst action of the pair of second porous electrodes 125 is weak and hence the current is smaller than in a normal state, that is, smaller than a normal-state value corresponding to the deterioration judgment reference value.

Therefore, whether the second pump cell 113 is in a deteriorated state can be judged by judging whether or not an oxygen partial pressure calculated on the basis of a second pump current Ip2 that is detected in a state that the oxygen partial pressure in the second measurement chamber 161 is set at the deterioration judgment reference value (in this embodiment, 13%) is equal to the deterioration judgment reference value.

At step S180 of the sensor diagnosis process, the gas sensor controller 190 calculates an oxygen pressure in the second measurement chamber 161 on the basis of a second pump current Ip2. If the oxygen pressure in the second measurement chamber 161 is equal to the deterioration judgment reference value, the gas sensor controller 190 judges that the second pump cell 113 is in a normal state. If the oxygen pressure in the second measurement chamber 161 is different from the deterioration judgment reference value, the gas sensor controller 190 judges that the second pump cell 113 is in a deteriorated state.

Capable of judging whether or not the second pump cell 113 is in a deteriorated state, the gas sensor controller 190 can judge whether or not the NOx gas sensor 10 having the various cells is in a deteriorated state.

In the embodiment, the gas sensor controller 190 corresponds to the above-mentioned term "sensor deterioration judging apparatus" and the oxygen partial pressure detection cell 112 corresponds to the above-mentioned term "oxygen partial pressure detection cell". The gas sensor controller 190 executing step S110 corresponds to the term "first pump current detecting unit," the gas sensor controller 190 executing step S120 corresponds to the term "status judging unit," the gas sensor controller 190 executing step S130 corresponds to the term "pump stopping unit," the gas sensor controller 190 executing step S170 corresponds to the term "second pump current detecting unit," and the gas sensor controller 190 executing step S180 corresponds to the term "deterioration judging unit."

The first pump cell 111 corresponds to the term "first oxygen ion pump cell" and the second pump cell 113 corresponds to the term "second oxygen ion pump cell."

Although the embodiment of the invention has been described above, the invention is not limited to the above embodiment at all and it goes without saying that various modifications are possible without departing from the technical scope of the invention.

For example, although in the above embodiment the judgment reference values used at steps S120 and S180 are set at 20% and 13%, respectively, a prescribed range (e.g., 20% or more) may be used instead of the one numerical value.

Although in the above embodiment the elapsed time judgment value used at step S150 is set at 500 ms, it is not limited to 500 ms and may be set at a time that is long enough for a gas atmosphere in the second measurement chamber 161 to become equivalent to a gas atmosphere in the first measurement chamber 159.

This application is based on Japanese Patent Application JP 2005-340537, filed Nov. 25, 2005, the entire content of which is hereby incorporated by reference, the same as if set forth at length.

What is claimed is:

1. A sensor deterioration judging apparatus for judging whether a gas sensor is in a deteriorated state, the gas sensor including:

a first measurement chamber into which a gas to be measured is introduced through a first diffusion resistor portion;

a first oxygen ion pump cell having a first oxygen ion conductor and first and second electrodes provided on the first oxygen ion conductor wherein the first electrode is arranged in the first measurement chamber which pumps oxygen into or out of the gas that has been introduced into the first measurement chamber to be measured;

a second measurement chamber into which the gas to be measured is introduced through a second diffusion resistor portion after having been subjected to oxygen pumping in the first measurement chamber;

a second oxygen ion pump cell having a second oxygen ion conductor and third and fourth electrodes provided on the second oxygen ion conductor so that the third electrode is provided in the second measurement chamber, wherein a current corresponding to a concentration of a particular gas in the second measurement chamber flows in the second oxygen ion pump cell;

a reference oxygen chamber set to have a reference oxygen partial pressure atmosphere; and an oxygen partial pressure detection cell having a third oxygen ion conductor and fifth and sixth electrodes provided on the third oxygen ion conductor wherein the fifth electrode is provided in the first measurement chamber and the sixth electrode is provided in the reference oxygen chamber, the sensor deterioration judging apparatus comprising:

a first pump current detecting unit, a status judging unit, a pump stopping unit, a second pump current detecting unit, a deterioration judging unit, and having a processor configured to detect a first pump current flowing through the first oxygen ion pump cell;

to determine an oxygen partial pressure of the gas to be measured on the basis of the first pump current, and to judge whether the determined oxygen partial pressure of the gas to be measured is equal to a preset status judgment reference value;

to stop the pumping in or out of oxygen that is being performed by the first oxygen ion pump cell when the status judging unit judges that the oxygen partial pressure of the gas to be measured is equal to the status judgment reference value which is equivalent to the oxygen partial pressure in the atmosphere;

to detect a second pump current flowing through the second oxygen ion pump cell after the pump stopping unit stops the pumping operation of the first oxygen ion pump cell; and to judge that the second oxygen ion pump cell is in a deteriorated state when an oxygen partial pressure in the second measurement chamber calculated on the basis of the second pump current differs from a deterioration judgment reference value that is set in advance on the basis of the status judgment reference value.

2. The sensor deterioration judging apparatus as claimed in claim 1, wherein the second pump current detecting unit detects a second pump current after a lapse of a stabilization standby time, the stabilization standby time being the time that the oxygen partial pressure in the second measurement chamber takes to become stable after the pumping operation of the first oxygen ion pump cell is stopped by the pump stopping unit.

3. A sensor deterioration judging method for judging whether a gas sensor is in a deteriorated state, the gas sensor including:

a first measurement chamber into which a gas to be measured is introduced through a first diffusion resistor portion;

a first oxygen ion pump cell having a first oxygen ion conductor and first and second electrodes arranged on the first oxygen ion conductor wherein the first electrode is provided in the first measurement chamber for pumping oxygen into or out of the gas to be measured that has been introduced into the first measurement chamber;

a second measurement chamber into which the gas to be measured after having been subjected to the oxygen pumping in the first measurement chamber;

a second oxygen ion pump cell having a second oxygen ion conductor and third and fourth electrodes provided on the second oxygen ion conductor wherein the third electrode is provided in the second measurement chamber so that a current corresponding to a concentration of a particular gas in the second measurement chamber flows in the second oxygen ion pump cell;

a reference oxygen chamber set to have a reference oxygen partial pressure atmosphere; and an oxygen partial pressure detection cell having a third oxygen ion conductor and fifth and sixth electrodes provided on the third oxygen ion conductor so that the fifth electrode is provided in the first measurement chamber and the sixth electrode is provided in the reference oxygen chamber, the sensor deterioration judging method comprising:

detecting a first pump current flowing through the first oxygen ion pump cell;

determining an oxygen partial pressure of the gas to be measured on the basis of the first pump current, and judging whether or not the determined oxygen partial pressure of the gas to be measured is equal to a preset status judgment reference value;

stopping the first oxygen ion pump cell from the pumping in or out of oxygen when the oxygen partial pressure of the gas to be measured is equal to the status judgment reference value which is equivalent to the oxygen partial pressure in the atmosphere;

detecting a second pump current flowing through the second oxygen ion pump cell after the pumping operation of the first oxygen ion pump cell is stopped; and judging that the second oxygen ion pump cell is in a deteriorated state when an oxygen partial pressure in the second measurement chamber that is calculated on the basis of the second pump current differs from a deterioration judgment reference value that is set in advance on the basis of the status judgment reference value.

4. A sensor deterioration judging method for judging whether a gas sensor is in a deteriorated state, comprising:

detecting a first pump current through a first pump cell;

determining an oxygen concentration in a gas to be measured based on the first pump current;

determining whether the oxygen concentration in the gas to be measured is equal to a status judgment reference value;

stop pumping oxygen into or out of a first measurement chamber when the oxygen concentration in the gas to be measured is equal to the status judgment reference value which is equivalent to the oxygen partial pressure in the atmosphere;

detecting a second pump current through a second pump cell;

determining an oxygen concentration in a second measurement chamber based on the second pump current;

determining whether the oxygen concentration in the second measurement chamber is equal to a deterioration judgment reference value; and determining that the second pump cell is in a deteriorated stated when the oxygen concentration in the second measurement chamber is different from the deterioration judgment reference value, wherein the deterioration judgment reference value is lower than the status judgment reference value.

* * * * *